United States Patent [19]

Parsons et al.

[11] Patent Number: 5,096,915
[45] Date of Patent: Mar. 17, 1992

[54] AZOLE FUNGICIDES

[75] Inventors: John H. Parsons, Essex; Donald J. Simpson, Suffolk; Philip J. Dudfield, Essex, all of England

[73] Assignee: Schering Agrochemicals, England

[21] Appl. No.: 500,390

[22] Filed: Mar. 28, 1990

[30] Foreign Application Priority Data

Mar. 28, 1989 [GB] United Kingdom ................. 8906965

[51] Int. Cl.$^5$ ................. A01N 43/50; C07D 233/90; C07D 233/94
[52] U.S. Cl. ..................... 514/398; 514/94; 514/399; 514/400; 548/111; 548/337; 548/338; 548/341
[58] Field of Search ............... 548/111, 337, 338, 339, 548/341, 342; 514/94, 398, 399, 400

[56] References Cited

FOREIGN PATENT DOCUMENTS 298196  1/1989  European Pat. Off. ............ 548/337

Primary Examiner—Patricia L. Morris
Attorney, Agent, or Firm—Ostrolenk, Faber, Gerb & Soffen

[57] ABSTRACT

The invention provides compounds of formula I

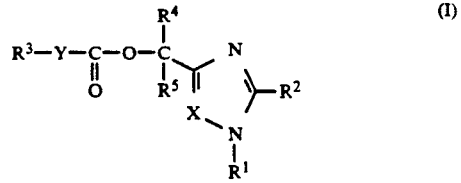

in which X, Y and $R^{1-5}$ are as defined in the description. The compounds have valuable fungicidal activity.

17 Claims, No Drawings

AZOLE FUNGICIDES

This invention relates to compounds having fungicidal activity.

In our EP284277 is disclosed fungicidal compounds of formula

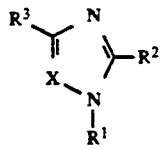

in which
X is $CR^4$ or N;
$R^1$ is $-SO_2R^5$,

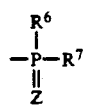

or $-COR^8$
$R^2$ is CN,

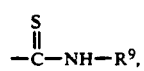

$-CH=N-OR^{10}$,

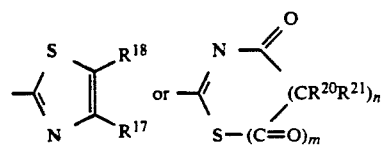

$R^3$ and $R^4$, may be the same or different and are alkyl, cycloalkyl, cycloalkenyl, alkenyl, alkynyl or amino, all of which are optionally substituted, hydrogen, halogen, hydroxy, cyano, nitro, acyl, $R^{11}SO_p$, $R^{12}O$ or aryl;

$R^5$ is aryl, optionally substituted alkyl or optionally substituted amino;

$R^6$ and $R^7$, may be the same or different and are amino, alkoxy or alkylthio, each of which is optionally substituted;

$R^8$ has the same meaning as $R^5$ or can be alkoxy, alkenyloxy, alkynyloxy or alkylthio, each of which is optionally substituted, or is aryloxy;

$R^9$ is hydrogen, optionally substituted alkyl, alkenyl, alkynyl, alkoxycarbonyl, acyl, aryl or cycloalkyl;

$R^{10}$ is hydrogen, optionally substituted alkyl, alkenyl, alkynyl, all of which are optionally substituted, or is aryl;

$R^{12}$ has the same meaning as R11 or is acyl;

$R^{17}$ is hydrogen, alkyl, alkoxycarbonyl, aryl or heteroaryl and $R^{18}$ is hydrogen or alkyl or $R^{17}$ and $R^{18}$ together with the carbons to which they are attached, form a benzo ring;

$R^{20}$ and $R^{21}$ may be the same or different and are hydrogen or alkyl;

Z is oxygen or sulphur;

m is 0 and n is 1 or 2 or m is 1 and n is 0 or 1; and p is 0 or 1.

In that patent, in most of the exemplified compounds, the $R^3$ group is a (substituted) phenyl. There is only one example of $R^3$ being substituted alkyl and this a compound where $R^3$ is trifluoromethyl. We have now found that particular group of compounds of this type, where $R^3$ is specified substituted alkyl have particularly valuable properties.

According to the invention there is provided a compound of formula I

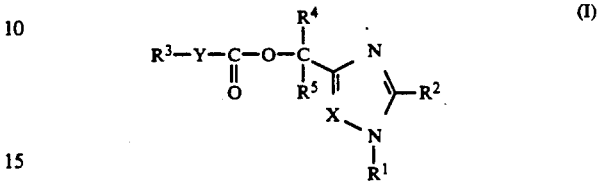

in which
X is $CR^6$ or N;
Y is O, S, $NR^{16}$ or represents a bond;
$R^1$ is $-SO_2R^7$,

or $-COR^{10}$
$R^2$ is CN,

or $-CH=N-OR^{12}$, $R^3$ is alkyl, cycloalkyl, alkenyl or alkynyl, all of which are optionally substituted, or is aryl;

$R^4$, $R^5$ and $R^{16}$ have the same meaning as $R^3$ or are hydrogen;

$R^6$ is alkyl, cycloalkyl, cycloalkenyl, alkenyl, alkynyl or amino, all of which are optionally substituted, hydrogen, halogen, hydroxy, cyano, nitro, acyl, $R^{13}SO_p$, $R^{14}O$ or aryl;

$R^7$ is aryl, optionally substituted alkyl or optionally substituted amino;

$R^8$ and $R^9$, may be the same or different and are amino, alkoxy or alkylthio, each of which is optionally substituted;

$R^{10}$ has the same meaning as $R^7$ or can be alkoxy, alkenyloxy, alkynyloxy or alkylthio, each of which is optionally substituted, or is aryloxy;

$R^{11}$ is hydrogen, optionally substituted alkyl, alkenyl, alkynyl, alkoxycarbonyl, acyl, aryl or cycloalkyl;

$R^{12}$ is hydrogen, or optionally substituted alkyl, alkenyl or alkynyl;

$R^{13}$ is alkyl, cycloalkyl, cycloalkenyl, alkenyl, alkynyl, all of which are optionally substituted, or is aryl;

$R^{14}$ has the same meaning as $R^{13}$ or is acyl;

Z is oxygen or sulphur; and is 0 or 1.

Alkyl groups are preferably of 1 to 8 carbon atoms, especially methyl; alkenyl and alkynyl groups are usually of 3 to 4 carbon atoms and cycloalkyl and cycloalkenyl groups are usually of 3 to 8 carbon atoms. Substituents, when present on any such group, include halogen, hydroxy, alkoxy and aryl. Aryl groups are usually phenyl, optionally substituted, e.g. by halogen, alkyl, alkoxy, nitro, cyano, $-COR^{10}$, optionally substituted sulphamoyl, optionally substituted amino, alkyl-$SO_q$, or aryl-$SO_q$, where q is 0, 1 or 2, and any alkyl or alkoxy group is optionally substituted.

The term aryl may include heteroaryl groups such as thienyl, furyl or pyridyl and can also include polynuclear aromatic groups, such as naphthyl and benzimidazolyl. Amino groups are usually substituted by one or more of the groups $R^{13}$, acyl, optionally substituted amino (including groups substituted through a double bond), hydroxy or optionally substituted alkoxy, or two substituents can form a ring, e.g. a morpholino or piperidino ring. Sulphamoyl groups can be substituted similarly to amino groups. The term acyl can include residues of both carboxylic and sulphonic acids and includes the groups $R^{15}(O)_rCO$ and $R^{15}SO_2$, where $R^{15}$ has the same meaning as $R^{13}$ or is optionally substituted amino and r is 0 or 1. It thus includes residues of carbamic and sulphamic acids. Acyl groups are preferably alkanoyl, aroyl, alkylsulphonyl, arylsulphonyl, N,N-dialkylsulphamoyl or N-alkyl-N-aryl-sulphamoyl, in which the alkyl groups are e.g. of 1 to 4 carbon atoms, and the alkyl and phenyl can be substituted as previously mentioned.

In a preferred group of compounds:

X is CH or N, especially CH;

Y is O, S, $NR^{16}$ or represents a bond and generally the last;

$R^1$ is dimethylsulphamoyl;

$R^2$ is cyano;

$R^3$ is phenyl, optionally substituted by one to three groups, selected from halogen, alkyl (especially methyl), trifluoromethyl, nitro and alkoxy (especially methoxy); and $R^4$, $R^5$ and $R^{16}$ are hydrogen.

The compounds of the invention have activity as fungicides, especially against fungal diseases of plants, e.g. downy mildews, especially vine downy mildew (*Plasmopara viticola*), and late tomato blight and potato blight (*Phytophthora infestans*). They are also active against powdery mildews, such as barley powdery mildew (*Erysiphe graminis*), as well as being active against diseases such as rice blast (*Pyricularia oryzae*) and apple scab (*Venturia inaequalis*). They may also have activity against other fungi, such as Botrytis spp., Puccinia spp., Rhizoctonia spp., Fusarium spp. and Pythium spp.

The invention thus also provides a method of combating fungi at a locus infested or liable to be infested therewith, which comprises applying to the locus a compound of formula I.

The invention also provides an agricultural composition comprising a compound of formula I in admixture with an agriculturally acceptable diluent or carrier.

The composition of the invention may of course include more than one compound of the invention.

In addition the composition can comprise one or more additional active ingredients, for example compounds known to possess plant-growth regulant, herbicidal, fungicidal,insecticidal or acaricidal properties.

Alternatively the compounds of the invention can be used in sequence with the other active ingredient.

The diluent or carrier in the composition of the invention can be a solid or a liquid optionally in association with a surface-active agent, for example a dispersing agent, emulsifying agent or wetting agent. Suitable surface-active agents include anionic compounds such as a carboxylate, for example a metal carboxylate of a long chain fatty acid; an N-acylsarcosinate; mono- or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl-aryl sulphonates such as alkyl-benzene sulphonates or lower alkyl-naphthalene sulphonates, e.g. butyl-naphthalene sulphonate; salts of sulphonated naphthalene-formaldehyde condensates; salts of sulphonated phenol-formaldehyde condensates; or more complex sulphonates such as the amide sulphonates, e.g. the sulphonated condensation product of oleic acid and N-methyl taurine or the dialkyl sulphosuccinates, e.g. the sodium sulphonate of dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g. sorbitan fatty acid esters, condensation products of such esters with ethylene oxide, e.g. polyoxyethylene sorbitan fatty acid esters, block copolymers of ethylene oxide and propylene oxide, acetylenic glycols such as 2,4,7,9-tetramethyl-5-decyne-4,7-diol, ethoxylated acetylenic glycols or ethoxylated tristyrylphenols.

Examples of a cationic surface-active agent include, for instance, an aliphatic mono-, di-, or polyamine as an acetate, naphthenate or oleate; an oxygen-containing amine such as an amine oxide or polyoxyethylene alkylamine; an amide-linked amine prepared by the condensation of a carboxylic acid with a di- or polyamine; or a quaternary ammonium salt.

The compositions of the invention can take any form known in the art for the formulation of agrochemicals, for example, a solution, a dispersion, an aqueous emulsion, a dusting powder, a seed dressing, (including coatings to form a seed pellet), a fumigant, a smoke, a bait, a dispersible powder, an emulsifiable concentrate or granules, e.g. water dispersible granulaes. Moreover it can be in a suitable form for direct application or as a concentrate or primary composition which requires dilution with a suitable quantity of water or other diluent before application.

An emulsifiable concentrate comprises a compound of the invention dissolved in a water-immiscible solvent which is formed into an emulsion with water in the presence of an emulsifying agent.

A dusting powder comprises a compound of the invention intimately mixed and ground with a solid pulverulent diluent, for example, kaolin.

A granular solid comprises a compound of the invention associated with similar diluents to those which may be employed in dusting powders, but the mixture is granulated by known methods. Alternatively it comprises the active ingredient absorbed or adsorbed on a pre-granular diluent, for example, Fuller's earth, attapulgite or limestone grit.

Wettable powders, granules or grains usually comprise the active ingredient in admixture with a suitable surfactant and an inert powder diluent such as china clay.

Another suitable concentrate is a flowable suspension concentrate which is formed by grinding the compound with water or other liquid, a wetting agent and a suspending agent.

The concentration of the active ingredient in the composition of the present invention, as applied to plants is preferably within the range of 0.0001 to 3.0 percent by weight, especially 0.001 to 1.0 percent by weight. In a primary composition the amount of active ingredient can vary widely and can be, for example, from 5 to 95 percent by weight of the composition.

In the method of the invention the compound is generally applied to seeds, plants or their habitat. Thus the compound can be applied directly to the soil before, at or after drilling so that the presence of active compound in the soil can control the growth of fungi which may attack seeds. When the soil is treated directly the active compound can be applied in any manner which allows it to be intimately mixed with the soil such as by spraying, by broadcasting a solid form of granules, or by applying the active ingredient at the same time as drilling by inserting it in the same drill as the seeds. A suitable application rate is within the range of from 0.005 to 10 kg per hectare, more preferably from 0.05 to 1 kg per hectare.

Alternatively the active compound can be applied directly to the plant by, for example, spraying or dusting either at the time when the fungus has begun to appear on the plant or before the appearance of fungus as a protective measure. In both such cases the preferred mode of application is by foliar spraying. It is generally important to obtain good control of fungi in the early stages of plant growth as this is the time when the plant can be most severely damaged. However a later application to combat late diseases such as Septoria spp., may be advantageous. The spray or dust can conveniently contain a pre- or post-emergence herbicide if this is thought necessary. Sometimes, it is practicable to treat the roots of a plant before or during planting, for example, by dipping the roots in a suitable liquid or solid composition. When the active compound is applied directly to the plant a suitable rate of application is from 0.001 to 5 kg. per hectare, preferably from 0.005 to 1 kg per hectare.

The compounds of the invention may be prepared, in known manner, in a variety of ways.

For example, the compounds may be prepared by acylating a compound of formula II

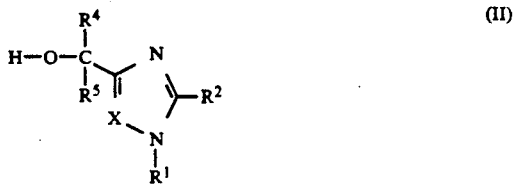

with a compound of formula III $$R^3-Y-CO-Q \qquad (III)$$

where Q is a leaving group, especially a halogen such as chlorine.

Compounds of formula II are generally known (e.g. as described in EP 284,277), or can be obtained in known manner. For example when $R^4$ and $R^5$ are both hydrogen the following reaction scheme can be adopted.

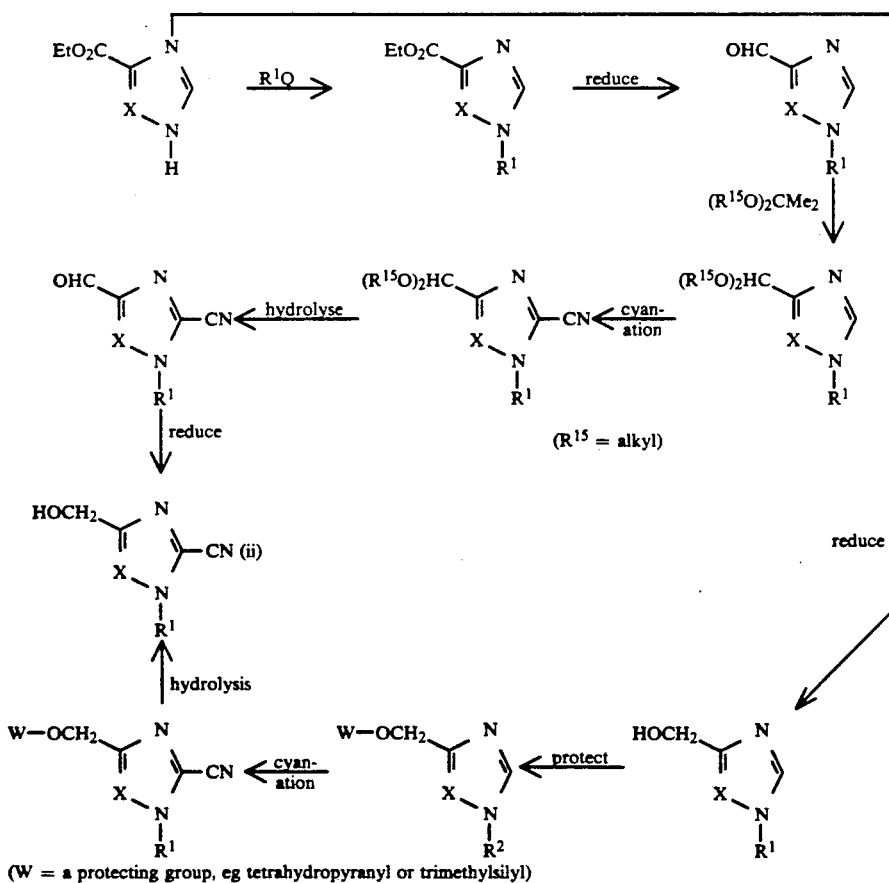

(W = a protecting group, eg tetrahydropyranyl or trimethylsilyl)

Cyanation can be achieved for instance by reacting the relevant compound with a compound Z—CN, where Z is a leaving group, such as cyano, p-tosyl or phenoxy. This reaction is generally carried out in the presence of a strong base and preferably an alkyl metal, such as butyllithium. The cyanation can also be carried out by (i) formylating an uncyanated compound, (e.g. using dimethylformamide in the presence of strong base, such as butyllithium) to give a compound having a formyl group (ii) treating this compound with hydroxylamine and (iii) subsequently dehydrating the oxime so obtained. Dehydration may be achieved using a reagent such as trifluoroacetic anhydride, phosphorus oxychloride or a chloroformate ester, usually under alkaline conditions. In the latter case an ester group may be substituted onto the 1-position a compound where $R^1$ is hydrogen.

Compounds, where $R^2$ is —CH=N—$OR^{12}$, can be obtained in a similar manner to steps (i) and (ii) above, using a compound of formula $H_2N$—$OR^{12}$.

Compounds of formula I, where $R^2$ is cyano, can be modified in known manner to give compounds where $R^2$ is thiocarbamoyl, by reaction with hydrogen sulphide and if desired modifying this group in known manner to give compounds where $R^9$ is not hydrogen. These reactions are usually carried out using a suitable acyl halide or isocyanate, for instance as described in EP 219192.

Sulphamoylation and similar reactions can be carried out, under basic conditions, e.g. in the presence of sodium hydride. Reductions can be carried out using conventional reducing agents and generally aluminium derivatives. Hydrolysis is usually carried out using a weak acid, such as acetic acid. The preparation of the acetal (which is used to protect the aldehyde in the subsequent cyanation) is carried out in conventional manner, e.g. using a 2,2-dialkoxypropane. Other protecting groups include tetrahydropyranyloxy.

The invention is illustrated in the following Examples. Structures of isolated novel compounds were confirmed by elemental and/or other appropriate analyses. Temperatures are in °C. and are uncorrected.

EXAMPLE 1

4-Chlorobenzoyl chloride (0.83 g) was added to a solution of 2-cyano-4-hydroxymethyl-1-(dimethylsulphamoyl)-imidazole (1.5 g) in dichloromethane (50 ml), containing triethylamine (1.0 ml) at 0°. The mixture was stirred for 45 minutes whilst the temperature was allowed to rise to room temperature. The mixture was added to water and the organic phase was separated, washed, dried and concentrated under reduced pressure. The residue was recrystallised from a mixture of diisopropyl ether and ethyl acetate to give 2-cyano-4-(4-chlorobenzoyloxy-methyl)-1-(dimethylsulphamoyl-)imidazole, m.p. 94≧-96°. (Compound 1)

In a similar manner the following compounds were obtained:

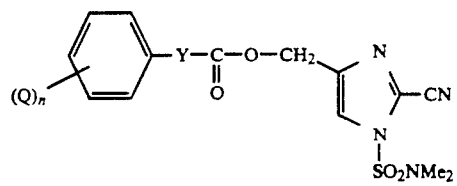

| Cpd no. | Y | $(Q)_n$ | m.p. (°) |
|---|---|---|---|
| 2 | — | 2-Cl | gum |
| 3 | — | 2,4-$Cl_2$ | 92-3 |
| 4 | — | 4-$NO_2$ | 118-9 |
| 5 | — | 2-$CF_3$ | gum |
| 6 | — | 3,4-$Cl_2$ | 118-9 |
| 7 | — | 3-$NO_2$ | 104-6 |
| 8 | — | 2,4-$F_2$ | 107-8 |
| 9 | — | 3-Cl | 91-3 |
| 10 | — | 4-$Bu^t$ | 104-6 |
| 11 | — | 4-Br | 90-2 |
| 12 | — | 4-CN | 138-40 |
| 13 | — | 4-$CF_3$ | 96-7 |
| 14 | — | 4-MeO | 107-9 |
| 15 | — | 2,4,6-$Me_3$ | 86-7 |
| 16 | NH | H | 104-5 |
| 17 | O | H | gum |

There was also obtained 4-acetyloxymethyl-2-cyano-1-(dimethylsulphamoyl)imidazole, m.p. 69≧-71°. (Compound 18)

The starting material was prepared as follows:

METHOD 1

A solution of ethyl imidazol-4-carboxylate (40.6 g) in tetrahydrofuran (500 ml) was treated with sodium hydride (9.14 g of 80% in oil), followed by dimethylsulphamoyl chloride (32.7 ml). The mixture was worked up to give crude ethyl 1-(dimethylsulphamoyl-)imidazole-4-carboxylate. Diisobutylaluminium hydride reduction gave 1-(dimethylsulphamoyl)-4-formylimidazole. This product (50 g) was stirred with Amberlyte IR-15 H+ resin (75 g) and methanol (2.5 ml) in 2,2-dimethoxypropane (250 ml) for 18 hours followed by three hours stirring with triethylamine (50 ml) and methanol (200 ml). The mixture was filtered and the filtrate worked up to give 1-(dimethylsulphamoyl)-4-(dimethoxymethyl)imidazole. A solution of this product (44.8 g) in dry tetrahydrofuran (350 ml) at −78° under a dry nitrogen atmosphere was treated with 2.5M butyllithium (35.7 ml) in hexane (2 ml). After stirring for 15 mins., tosyl cyanide (1.1 equivalents) was added and the reaction flask placed in an ice bath. The mixture was stirred for 30 mins., poured into water and the precipitate filtered and washed with ethyl acetate. The filtrate was worked up to give 2-cyano-1-(dimethylsulphamoyl)-4-(dimethoxymethyl)imidazole. This was hydrolysed with aqueous acetic acid to give 2-cyano-1-(dimethylsulphamoyl)-4-formylimidazole, which was treated to a diisobutylaluminium hydride reduction to give the starting material.

METHOD 2

Crude ethyl 1-(dimethylsulphamoyl)imidazole-4-carboxylate, from method 1, was reduced with diisobutylaluminium hydride to give 4-hydroxymethyl-1-(dimethylsulphamoyl)-imidazole. A mixture of this product (1.09 g) in methylene chloride (10 ml), dihydropyran (1.0 ml), pyridinium tosylate (1.26 g) and a few crystals of tosic acid was stirred at room temperature for 60 hours. Solvent was removed and the residue worked up to give 1-(dimethylsulphamoyl)-4-(tetrahydropyran-2-yloxy)imidazole, as an oil. This was cyanated with tosyl cyanide and butyllithium as described above to give 2-cyano-1-(dimethylsulphamoyl)-4-(tetrahydropyran-2-yloxy)imidazole, as an oil. A solution of this (150 mg) in ethanol (3 ml) was heated under reflux for 5 minutes after addition of a few milligrams of pyridinium tosylate. Solvent was removed and the residue purified by silica gel chromatography to give the starting material.

METHOD 3

A solution of 1-(dimethylsulphamoyl)-4-hydroxymethyl-imidazole (102.5 g) dry tetrahydrofuran (1 L) was stirred at 0°-5° C. while sodium hydride (15 g of 80% in oil) was added. A white solid formed over ½ hour. This suspension was treated, slowly, with trimethylsilyl chloride (63.5 ml) keeping the temperature at 0°-5° C. The white precipitate soon dispersed and after stirring for 1 hour the mixture was cooled to −70° C. in a dry ice/acetone bath. Butyllithium (2.5M in hexane; 200 ml) was added so that the temperature was maintained below −60° C. This mixture was stirred at −70° C. for ½ hour, then allowed to warm to −30° C. before phenyl cyanate (59.5 g) was added all in one go. The temperature rose to about −10° C. The solution was stirred at <0° C. for ½ hour then recooled to −70° C. and quenched carefully with 2M hydrochloric acid (250 ml). The mixture was allowed to warm to room temperature, then the organic layer was separated and concentrated to an orange oil. This oil was dissolved in ethyl acetate and combined with the ethyl acetate extracts of the remaining aqueous layer. This was washed with water, then with brine and finally separated then dried over magnesium sulphate. Evaporation of the solvent gave an orange oil which was purified by flash column chromatography to give the starting material.

TEST EXAMPLE

The compounds of the invention were subjected to various tests.

Compounds are assessed for activity against *Phytophthora infestans* (late tomato blight—PI) and *Plasmopara viticola* (vine downy mildew—PV).

Aqueous solutions or dispersions of the compounds at the desired concentration, including a wetting agent, were sprayed onto the appropriate plant and then inoculated by spraying with spore suspensions of the fungi. Plants were then kept under controlled environment conditions suitable for maintaining plant growth and development of the disease. After an appropriate time, the degree of infection of the leaf surface was visually estimated. Compounds were considered active if they gave greater than 50% control of the disease at a concentration of 125 ppm (w/v) or less. Compounds 1-5, 7-15 and 18 were active against *Phytophthora infestans* and compounds 1-8 and 10-15 were active against *Plasmopara viticola*.

We claim:

1. A compound of formula I $$R^3-Y-\underset{O}{\overset{\|}{C}}-O-\underset{R^5}{\overset{R^4}{\underset{|}{C}}}\begin{array}{c}N\\\|\\X\end{array}\!\!\!\!\!\!\!\!\!\!\!\!\begin{array}{c}\\\\ \\N\\|\\R^1\end{array}\!\!\!\!\!\!\!\!\!\!\!\!\!\!\!\!\!\!\!\!\!-R^2 \qquad (I)$$

in which
X is $CR^6$;
Y is O, S, $NR^{16}$ or represents a bond;
$R^1$ is $-SO_2R^7$, $$-\underset{Z}{\overset{R^8}{\underset{|}{P}}}-R^9$$

or $-COR^{10}$
$R^2$ is CN, $$-\overset{S}{\underset{\|}{C}}-NH-R^{11}$$

or $-CH=N-OR^{12}$,
$R^3$ is alkyl, cycloalkyl, alkenyl, alkynyl or phenyl, all of which are optionally substituted;
$R^4$, $R^5$ and $R^{16}$ have the same meaning as $R^3$ or are hydrogen;
$R^6$ is alkyl, cycloalky, cycloalkenyl, alkenyl, alkynyl, phenyl or amino, all of which are optionally substituted, hydrogen, halogen, hydroxy, cyano, nitro, $C_{1-4}$ alkanoyl, $R^{13}O_p$, or $R^{14}O$;
$R^7$ is optionally substituted alkyl, phenyl or amino;
$R^8$ and $R^9$, may be the same or different and are amino, alkoxy or alkylthio, each of which is optionally substituted;
$R^{10}$ has the same meaning as $R^7$ or can be alkoxy, alkenyloxy, alkynyloxy, phenoxy or alkylthio, each of which is optionally substituted;
$R^{11}$ is hydrogen, optionally substituted alkyl, alkenyl, alkynyl, alkoxycarbonyl, $C_{1-4}$ alkanoyl, phenyl or cycloalkyl;
$R^{12}$ is hydrogen, or optionally substituted alkyl, alkenyl or alkynyl;
$R^{13}$ is alkyl, cycloalkyl, cycloalkenyl, alkenyl, alkynyl or phenyl, all of which are optionally substituted;
$R^{14}$ has the same meaning as $R^{13}$ or is $C_{1-4}$ alkanoyl;
Z is oxygen or sulphur; and
p is 0 or 1
wherein any alkyl moiety has 1 to 8 carbon atoms, any alkenyl or alkynyl moiety has 3 to 4 carbon atoms, any cycloalkyl or cycloalkenyl moiety has 3 to 8 carbon atoms and any optional substituent is selected from the group consisting of halogen, hydroxy, hydroxy, alkoxy and phenyl and additionally in the case of optionally substituted phenyl, alkyl, nitro, cyano and trifluoromethyl.

2. A fungicidal composition comprising a fungicidally effective amount of a compound as claimed in claim 1, in admixture with an agriculturally acceptable diluent or carrier.

3. A method of combating phytopathogenic fungi which comprises applying to the fungus a fungicidally effective amount of or its locus a compound claimed in claim 1.

4. A compound according to claim 1 in which X is CH; Y is O, S, $NR^{16}$ or a bond; $R^1$ is dimethyl sulphamoyl; $R^2$ is cyano; $R^3$ is optionally substituted phenyl; and $R^4$, $R^5$ and $R^{16}$ are hydrogen.

5. A compound according to claim 4 in which Y is a bond and $R^3$ is phenyl substituted by 1 to 3 groups selected from the group consisting of halogen, alkyl, trifluoromethyl, nitro and alkoxy.

6. A compound according to claim 5 in which the substituents on the phenyl group are selected from the group consisting of chloro, bromo, trifluoromethyl, methyl, tert-butyl, nitro and methoxy.

7. A compound according to claim 6 in which $R^3$ is 4-chlorophenyl.

8. A fungicidal composition comprising a fungicidally effective amount of a compound as claimed in claim 4, in admixture with an agriculturally acceptable diluent or carrier.

9. A fungicidal composition comprising a fungicidally effective amount of a compound as claimed in claim 5, in admixture with an agriculturally acceptable diluent or carrier.

10. A fungicidal composition comprising a fungicidally effective amount of a compound as claimed in claim 6, in admixture with an agriculturally acceptable diluent or carrier.

11. A fungicidal composition comprising a fungicidally effective amount of a compound as claimed in claim 7, in admixture with an agriculturally acceptable diluent or carrier.

12. A fungicidal composition comprising a fungicidally effective amount of a compound as claimed in claim 8, in admixture with an agriculturally acceptable diluent or carrier.

13. A method of combating phytopathogenic fungi which comprises applying to the fungus or its locus a fungicidally effective amount of a compound claimed in claim 4.

14. A method of combating phytopathogenic fungi which comprises applying to the fungus or its locus a fungicidally effective amount of a compound claimed in claim 5.

15. A method of combating phytopathogenic fungi which comprises applying to the fungus or its locus a fungicidally effective amount of a compound claimed in claim 6.

16. A method of combating phytophathogenic fungi which comprises applying to the fungus or its locus a fungicidally effective amount of a compound claimed in claim 7.

17. A method of combating phytopathogenic fungi which comprises applying to the fungus or its locus a fungicidally effective amount of a compound claimed in claim 8.

* * * * *